(12) United States Patent
Wada

(10) Patent No.: US 11,511,083 B2
(45) Date of Patent: Nov. 29, 2022

(54) INTRODUCER SHEATH

(71) Applicant: TERUMO KABUSHIKI KAISHA, Tokyo (JP)

(72) Inventor: Satoshi Wada, Shizuoka (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 864 days.

(21) Appl. No.: 16/288,394

(22) Filed: Feb. 28, 2019

(65) Prior Publication Data
US 2019/0192826 A1 Jun. 27, 2019

Related U.S. Application Data

(63) Continuation of application No. PCT/JP2017/030784, filed on Aug. 28, 2017.

(30) Foreign Application Priority Data

Sep. 1, 2016 (JP) .............................. JP2016-171038

(51) Int. Cl.
*A61M 25/06* (2006.01)
*A61B 17/34* (2006.01)
(Continued)

(52) U.S. Cl.
CPC ........ *A61M 25/0662* (2013.01); *A61M 25/06* (2013.01); *A61B 17/3415* (2013.01);
(Continued)

(58) Field of Classification Search
CPC .............. A61M 25/0662; A61M 25/06; A61M 25/0097; A61M 39/22; A61M 2025/0681; A61B 17/3415
(Continued)

(56) References Cited

U.S. PATENT DOCUMENTS 4,838,280 A 6/1989 Haaga
5,254,105 A 10/1993 Haaga
(Continued)

FOREIGN PATENT DOCUMENTS

CN 1461204 A 12/2003
CN 1972726 A 5/2007
(Continued)

OTHER PUBLICATIONS

An English Translation of the International Search Report (Form PCT/ISA/210) and the Written Opinion of the International Searching Authority (Form PCT/ISA/237) dated Nov. 28, 2017, by the Japanese Patent Office in corresponding International Application No. PCT/JP2017/030784. (6 pages).

(Continued)

*Primary Examiner* — Phillip A Gray
(74) *Attorney, Agent, or Firm* — Buchanan Ingersoll & Rooney PC

(57) ABSTRACT

An introducer sheath is disclosed configured to be percutaneously inserted into a biological lumen and can shorten the time required for hemostasis at a wound site and lessen the physical burden on the patient after withdrawal of the introducer sheath. The introducer sheath includes a catheter body to be percutaneously introduced into a biological lumen, a hub configured to be connected to the proximal side of the catheter body, and a drug part that has a hemostatic agent capable of treating a wound site in biological tissue. The drug part is disposed at the proximal side of an outer surface of the catheter body.

19 Claims, 10 Drawing Sheets

(51) Int. Cl.
   *A61M 25/00* (2006.01)
   *A61M 39/22* (2006.01)
(52) U.S. Cl.
   CPC ......... *A61M 25/0097* (2013.01); *A61M 39/22* (2013.01); *A61M 2025/0681* (2013.01)
(58) Field of Classification Search
   USPC .................................................. 604/164.01
   See application file for complete search history.

(56) References Cited

U.S. PATENT DOCUMENTS

| | | | |
|---|---|---|---|
| 5,290,310 A * | 3/1994 | Makower | A61B 17/0057 |
| | | | 128/DIG. 8 |
| 5,728,133 A | 3/1998 | Kontos | |
| 5,911,715 A | 6/1999 | Berg et al. | |
| 8,262,625 B1 | 9/2012 | Fischell et al. | |
| 9,089,335 B2 | 7/2015 | Okamura | |
| 2007/0282265 A1 | 12/2007 | Shigematsu et al. | |
| 2010/0228185 A1 | 9/2010 | Roorda et al. | |
| 2011/0190697 A1 | 8/2011 | Farnan | |
| 2011/0282286 A1 | 11/2011 | Argentine | |
| 2014/0114286 A1 | 4/2014 | Okamura | |
| 2015/0032118 A1 | 1/2015 | Okamura et al. | |
| 2016/0008588 A1 | 1/2016 | Wada | |
| 2016/0361517 A1 | 12/2016 | Yazaki | |

FOREIGN PATENT DOCUMENTS

| | | |
|---|---|---|
| CN | 102892455 A | 1/2013 |
| CN | 103619399 A | 3/2014 |
| CN | 204485033 U | 7/2015 |
| CN | 105073175 A | 11/2015 |
| EP | 1 307 141 A2 | 5/2003 |
| JP | H06510460 A | 11/1994 |
| JP | H07506513 A | 7/1995 |
| JP | H10295699 A | 11/1998 |
| JP | 2009-232916 A | 10/2009 |
| WO | 02/09591 A2 | 2/2002 |
| WO | 2011122488 A1 | 10/2011 |
| WO | 2014/123381 A1 | 8/2014 |
| WO | 2015/133281 A1 | 9/2015 |

OTHER PUBLICATIONS

International Search Report (PCT/ISA/210) and Written Opinion (PCT/ISA/237) dated Nov. 28, 2017, by the Japanese Patent Office as the International Searching Authority for International Application No. PCT/JP2017/030784.

The extended European Search Report dated May 8, 2020, by the European Patent Office in corresponding European Patent Application No. 17846432.7-132. (8 pages).

Office Action (Notification of the First Office Action) dated Dec. 4, 2020, by the National Intellectual Property Administration, PRC in corresponding Chinese Patent Application No. 201780053589.3 and an English Translation of the Office Action. (15 pages).

Office Action (First Examination Report) dated Dec. 4, 2020, by the Patent Office, Government of India, in corresponding India Patent Application No. 201917007634 with an English Translation of the Office Action. (6 pages).

* cited by examiner

INTRODUCER SHEATH

CROSS-REFERENCES TO RELATED APPLICATIONS

This application is a continuation of International Application No. PCT/JP2017/030784 filed on Aug. 28, 2017, which claims priority to Japanese Application No. 2016-171038 filed on Sep. 1, 2016, the entire content of both of which is incorporated herein by reference.

TECHNICAL FIELD

The present disclosure generally relates to an introducer sheath used for an introducer assembly as a medical instrument.

BACKGROUND DISCUSSION

Procedures for percutaneously introducing various catheters and the like into living bodies are performed in the medical field.

An introducer sheath provided with a catheter body to be percutaneously introduced into a biological lumen and a hub connected to the proximal side of the catheter body is used in such procedures (see, for example, International Publication (WO) No. 2011/122488).

The introducer sheath forms an access path interconnecting the inside of a living body and the outside of the living body as a result of the percutaneous catheter body introduction into the biological lumen.

The introducer sheath is withdrawn after a procedure for percutaneously introducing the catheters and the like into the living body (hereinafter, referred to as the desired procedure).

After the introducer sheath is withdrawn, hemostasis needs to be performed at the site where the introducer sheath was introduced (hereinafter, referred to as the wound site).

Wound site compression is widely used as an example of methods for the hemostasis. A balloon or the like that is inflated as a result of fluid injection is used during the compression.

Prolonged wound site compression for hemostasis may be physically burdensome on a patient.

Desired in this regard is a technique for lessening a patient's physical burden related to hemostasis at the wound site.

SUMMARY

An introducer sheath is disclosed that is percutaneously inserted into a biological lumen and can shorten the time required for hemostasis at the wound site and can lessen or reduce the physical burden on the patient after withdrawal of the introducer sheath.

One aspect of the disclosure involves an introducer sheath that includes a catheter body to be percutaneously introduced into a biological lumen, a hub connected to a proximal side of the catheter body, and a drug part having a hemostatic agent capable of treating a wound site in biological tissue. The drug part is disposed on a proximal side of an outer surface of the catheter body.

The introducer sheath according to the disclosure is provided with the drug part having the hemostatic agent capable of treating the wound site in the biological tissue. The drug part is disposed on the proximal side of the outer surface of the catheter body.

By the drug part being disposed on the proximal side of the outer surface of the catheter body, the introducer sheath can be percutaneously introduced into the biological lumen and the desired procedure can be performed without contact between the biological tissue and the drug part.

After the desired procedure is completed, the proximal side of the catheter body is inserted into the wound site. As a result, at least a part of the drug part can be brought into contact with the wound site.

The proximal side of the catheter body is withdrawn from the wound site with at least a part of the drug part in contact with the wound site. Then, at least a part of the drug part can be placed at the wound site.

Since the drug part has the hemostatic agent, hemostasis at the wound site can be promoted by at least a part of the drug part being brought into contact with and placed at the wound site.

Accordingly, after withdrawal of the introducer sheath percutaneously introduced into a biological lumen, the time required for hemostasis at the wound site can be shortened and the physical burden on the patient can be lessened.

In accordance with another aspect, an introducer sheath is disclosed comprising: a catheter body configured to be percutaneously introduced into a biological lumen; a hub configured to be connected to a proximal side of the catheter body; a drug part having a hemostatic agent capable of treating a wound site in biological tissue, and wherein the drug part is disposed on a proximal side of an outer surface of the catheter body; a strain relief covering a distal portion of the hub and surrounding a predetermined range of the proximal side of the catheter body, and wherein the drug part is disposed in the predetermined range of the catheter body surrounded by the strain relief; and a groove portion recessed toward an inner space of the catheter body, the groove portion being provided over the entire circumference of the outer surface of the catheter body in a range closer to the proximal side of the catheter body than a most distal portion of the strain relief and closer to a distal side of the catheter body than the distal portion of the hub.

In accordance with a further aspect, a method is disclosed for treating a wound site resulting from treatment of a biological lumen, the method comprising: introducing an introducer sheath into the wound site of a patient, the introducer sheath including a catheter body percutaneously introduced into the biological lumen, a hub connected to a proximal side of the catheter body, and a drug part having a hemostatic agent capable of treating the wound site in the biological tissue and located on an outer surface of the catheter body; placing the catheter body in the biological lumen in a state where the drug part is not disposed at the wound site; performing desired treatment by introducing a treatment instrument into the biological lumen via the introducer sheath in a state where the drug part is not disposed at the wound site and the catheter body is placed at the wound site; bringing at least a part of the drug part into contact with the wound site by moving the catheter body toward the wound site after the desired treatment is completed; and placing the at least a part of the drug part at the wound site.

BRIEF DESCRIPTION OF THE DRAWINGS

FIG. 5A is a diagram illustrating how puncturing is performed with an introduction needle, FIG. 5B is a diagram illustrating how a guide wire is inserted into a biological lumen, FIG. 5C is a diagram illustrating a state where the guide wire is placed in the biological lumen, FIGS. 5D and 5E are diagrams illustrating how puncturing is performed with the introducer assembly, and FIG. 5F is a diagram illustrating a state where the introducer sheath is placed in the biological lumen.

DETAILED DESCRIPTION

First Embodiment

Hereinafter, an introducer assembly 10 according to the present embodiment will be described with reference to accompanying drawings.

FIGS. 1 to 4 are diagrams illustrating each part of the introducer assembly 10, and FIGS. 5A to 7 are diagrams illustrating a treatment method using an introducer sheath 100.

Figure 2:
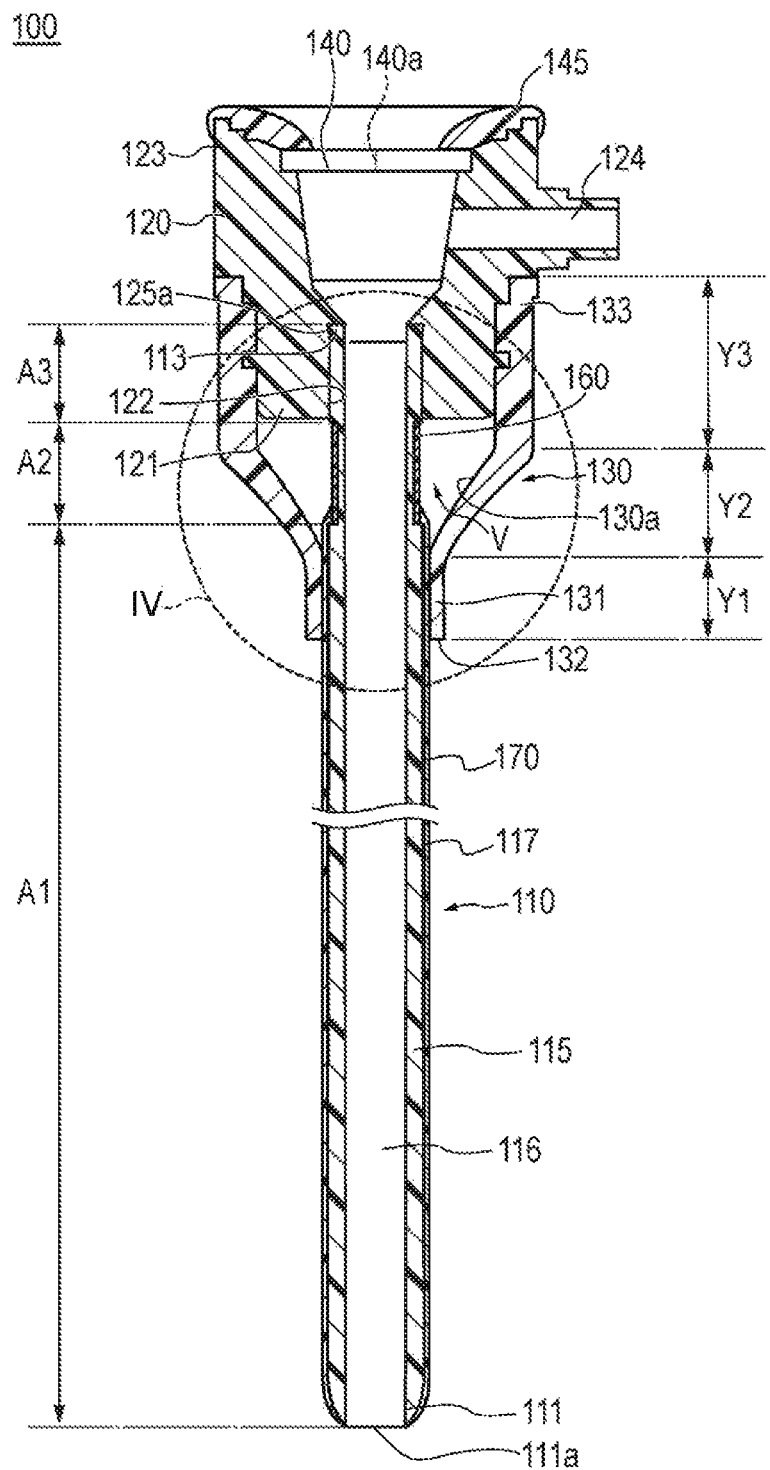
FIG. 2 is a cross-sectional view of an introducer sheath according to the first embodiment.

Referring to FIG. 2, in this specification, the side on which a hub (hub) 120 is disposed in the introducer sheath 100 (upper side in FIG. 2) is referred to as the "proximal side". The side that is introduced into a biological lumen R and located on the side opposite to the proximal side in the introducer sheath 100 (lower side in FIG. 2) is referred to as the "distal side". The direction in which the introducer sheath 100 extends (upward-downward direction in FIG. 2) is referred to as the "axial direction". The "distal portion" includes the distal end (most distal end) and the vicinity of the distal end (most distal end), and the "proximal portion" includes the proximal end (most proximal end) and the vicinity of the proximal end (most proximal end).

Figure 6A:
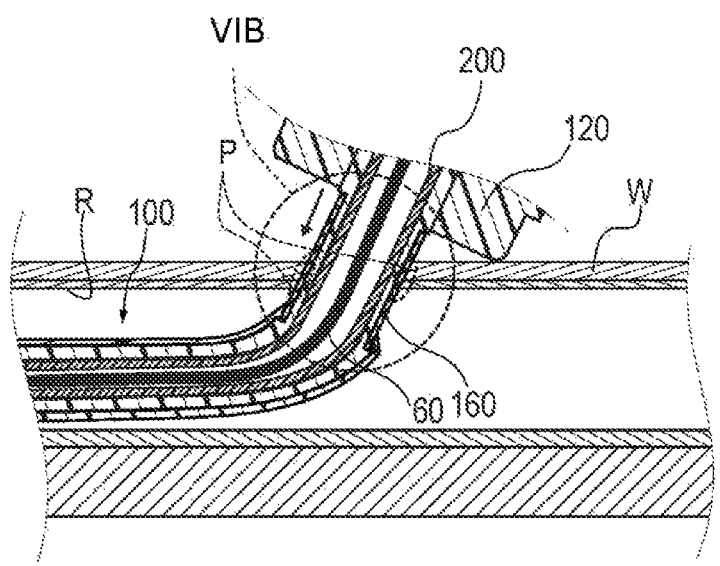
FIG. 6A is a schematic cross-sectional view illustrating how a drug part is introduced into a wound site.
Figure 6B:
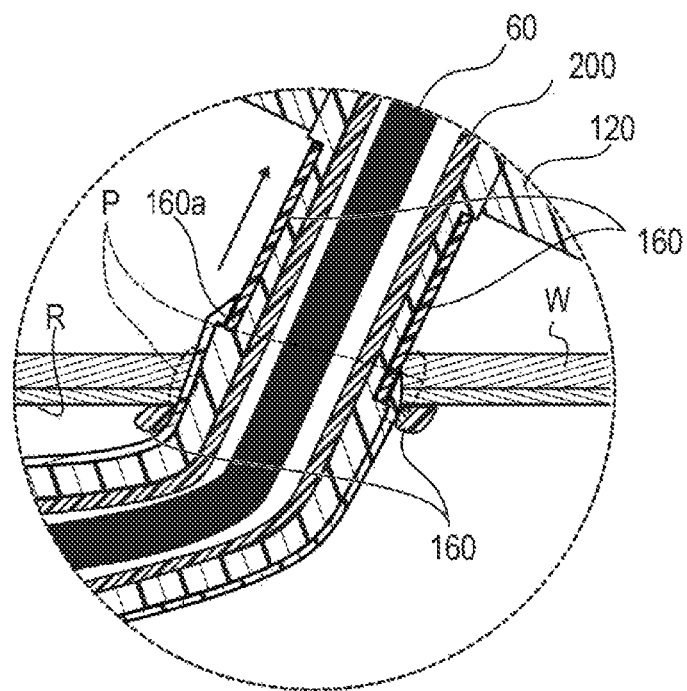
FIG. 6B is an enlarged view illustrating the dashed-line portion VIB in FIG. 6A and a diagram illustrating how a hemostatic agent is placed at the wound site.
Figure 7:
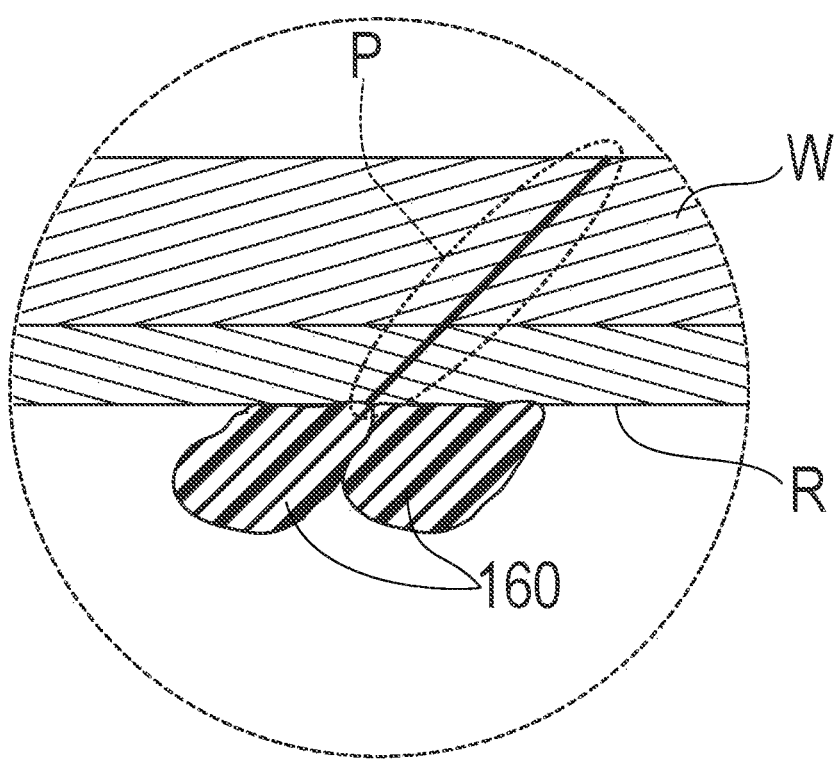
FIG. 7 is a diagram illustrating a state where the hemostatic agent is placed at the wound site.

Referring to FIGS. 6A and 6B, a site P in biological tissue W wounded by the introducer sheath 100 being percutaneously introduced into the biological lumen R is referred to as the "wound site".

Figure 1:
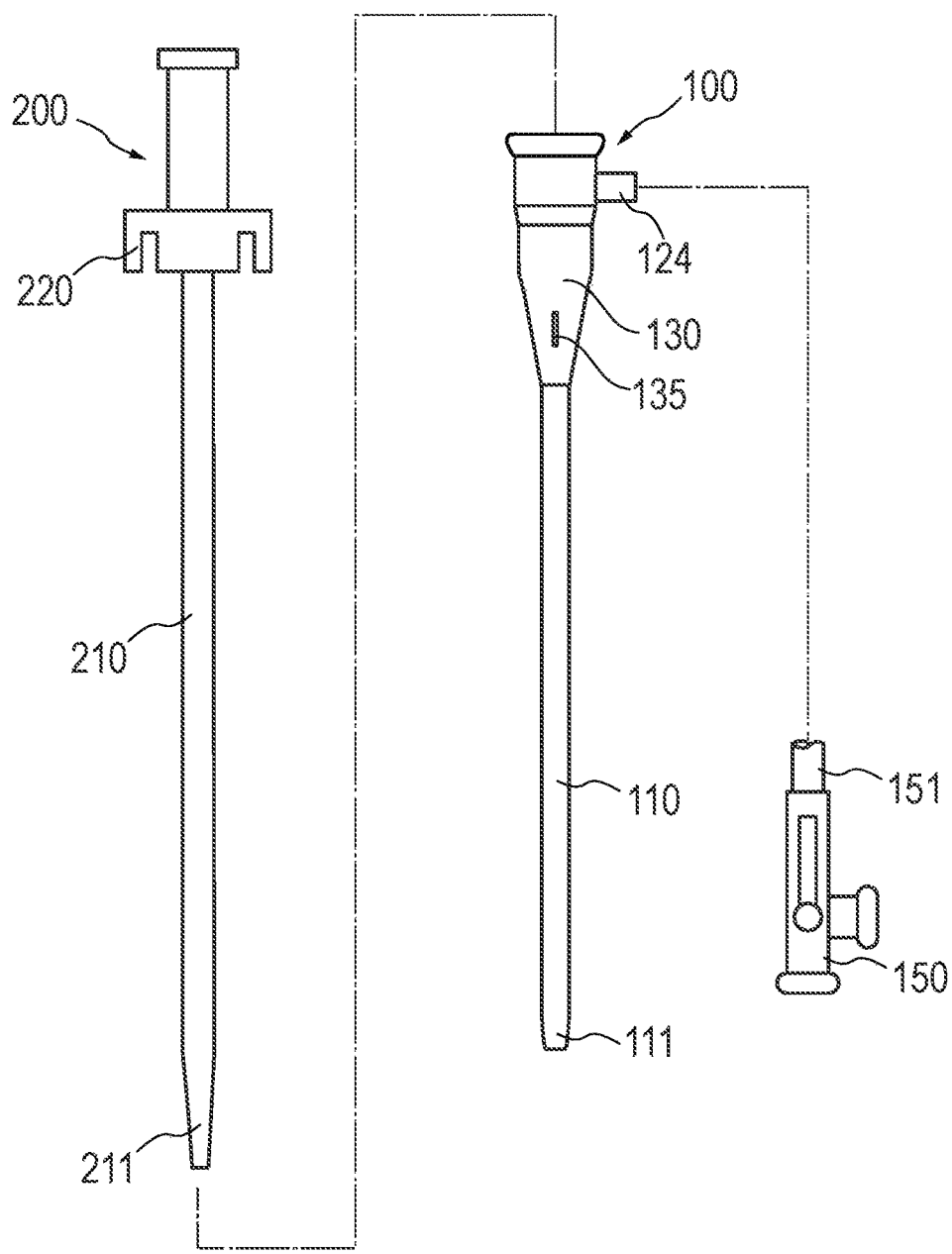
FIG. 1 is a diagram illustrating an introducer assembly according to a first embodiment.

As illustrated in FIG. 1, the introducer assembly 10 according to the present embodiment includes the introducer sheath 100 and a dilator 200.

The introducer sheath 100 and the dilator 200 will be described in detail below.

In accordance with an exemplary embodiment, the introducer sheath 100 is placed in the biological lumen R such as a blood vessel and used so that treatment instruments such as a catheter and a guide wire are inserted through a lumen 116 and the treatment instruments are introduced into the biological lumen R. A procedure such as percutaneous coronary intervention (PTCA/PCI) (hereinafter, referred to as the desired procedure) can be performed by means of the guide wire or the like introduced into the biological lumen R. Approach methods for the percutaneous coronary intervention include trans femoral intervention (TFI) for introducer sheath introduction from a foot and trans radial intervention (TRI) for introducer sheath introduction from an arm.

Figure 5A:
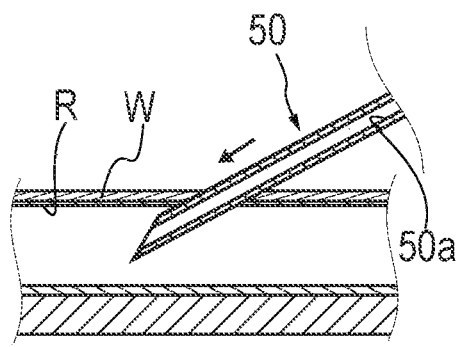
FIGS. 5A-5F are schematic cross-sectional views illustrating a treatment method using the introducer according to the first embodiment, where
Figure 5B:
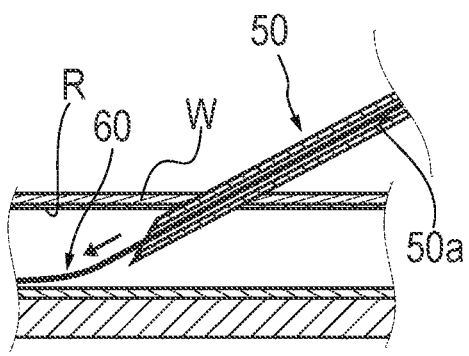
Figure 5C:
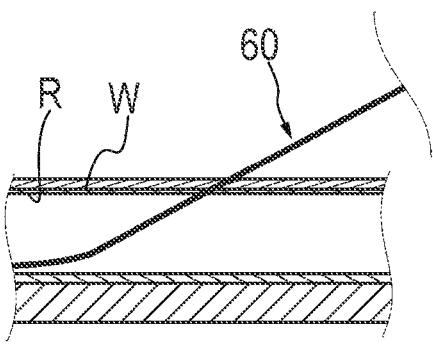
Figure 5D:
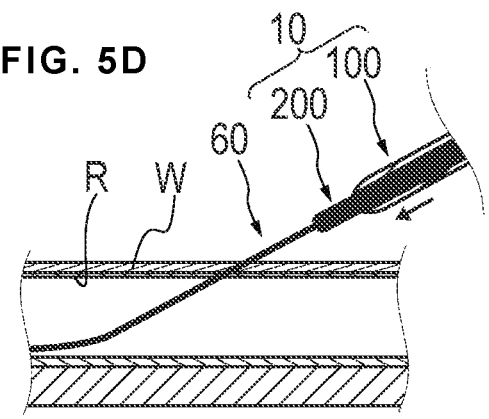
Figure 5E:
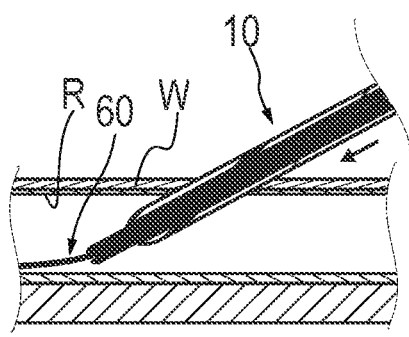
Figure 5F:
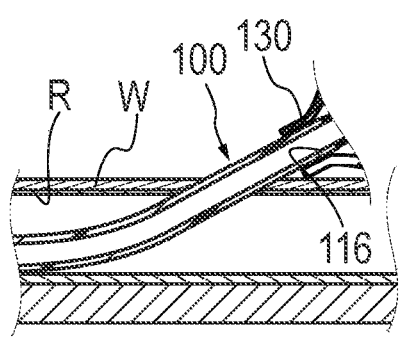

Referring to FIGS. 2 and 5F, the introducer sheath 100 can include a catheter body 110 to be percutaneously introduced into the biological lumen R, the hub 120 connected to the proximal side of the catheter body 110, and a drug part 160 having a hemostatic agent capable of treating the wound site P in the biological tissue W. The drug part 160 is disposed on the proximal side of an outer surface 117 of the catheter body 110. The introducer sheath 100 further includes a strain relief (or strain relief device) 130 covering a distal portion 121 of the hub 120 and surrounding a predetermined range of the proximal side of the catheter body 110.

In accordance with an exemplary embodiment, a substantially cylindrical tubular member in which the lumen 116 extends constitutes the catheter body 110. As illustrated in FIG. 2, the catheter body 110 has a tapered distal portion 111, a main body portion 115 located on the proximal side of the distal portion 111, and a proximal portion 113 located on the proximal side of the main body portion 115 and connected to the hub 120.

The catheter body 110 material is not particularly limited. Examples of the catheter body 110 material can include polymer materials such as polyolefin (for example, polyethylene, polypropylene, polybutene, ethylene-propylene copolymer, ethylene-vinyl acetate copolymer, ionomer, and mixture of at least two of the six), polyolefin elastomer, crosslinked polyolefin, polyvinyl chloride, polyimide, polyimide elastomer, polyester, polyester elastomer, polyurethane, polyurethane elastomer, fluororesin, polycarbonate, polystyrene, polyacetal, polyimide, polyetherimide, and polyether ether ketone and mixtures of the polymer materials.

A hydrophilic lubricating layer 170 for providing surface lubricity during wetting is disposed on the outer surface 117 of the catheter body 110. The material of hydrophilic lubricating layer 170 can be a material exhibiting hydrophilicity and swellability when brought into contact with an aqueous solvent. In accordance with an exemplary embodiment, a layer containing a hydrophilic lubricating layer 170 material that exhibits hydrophilicity and lubricity (surface lubricity) can be used when the catheter body 110 is inserted into a living body. Accordingly, the catheter body 110 on which the hydrophilic lubricating layer 170 is disposed can be smoothly inserted into a living body and is capable of improving operability for an operator. In a case where the catheter body 110 is inserted into a body cavity such as a blood vessel, tissue damage can be reduced and a patient's burden can be lessened by means of the hydrophilicity and lubricity (surface lubricity).

As set forth above, the hydrophilic lubricating layer 170 material is not particularly limited insofar as the material exhibits hydrophilicity and swellability when brought into contact with an aqueous solvent. Known materials can be used as the material. For example, the hydrophilic lubricating layer 170 material can include a copolymer of epoxy group-containing monomer such as glycidyl acrylate, glycidyl methacrylate, 3,4-epoxycyclohexylmethyl acrylate, 3,4-epoxycyclohexylmethyl methacrylate, β-methyl glycidyl methacrylate, and allyl glycidyl ether and hydrophilic monomer such as N-methyl acrylamide, N, N-dimethylacrylamide, and acrylamide; a (co)polymer composed of the hydrophilic monomer; a cellulose-based polymer substance such as hydroxypropyl cellulose and carboxymethyl cellulose; and polysaccharide, polyvinyl alcohol, methyl vinyl ether-maleic anhydride copolymer, water-soluble polyamide, poly (2-hydroxyethyl (meth) acrylate), polyethylene glycol, polyacrylamide, polyvinylpyrrolidone, and the copolymer of polyvinylpyrrolidone and polyurethane described in U.S. Pat. No. 4,100,309 and JP-A-59-19582. In accordance with an exemplary embodiment, a single material may constitute the hydrophilic lubricating layer 170. Alternatively, a mixture of two or more lubricating layer 170 materials may constitute the hydrophilic lubricating layer 170.

Referring to FIG. 2, the hub 120 has a lumen 122 to which the proximal portion 113 of the catheter body 110 is fixed and a side port 124 communicating with the lumen 122. One end of a flexible tube 151 (see FIG. 1) is liquid-tightly connected to the side port 124. In accordance with an exemplary embodiment, a three-way stopcock 150 or the like can be attached to the other end of the tube 151. A liquid such as a saline solution can be injected from a port of the three-way stopcock 150 into the lumen 116 of the catheter body 110 via the tube 151. The tube 151 can be made from a material such as polyvinyl chloride or the like.

Although the hub 120 material is not particularly limited, a hard material such as a hard resin is preferable. Specific examples of the hard resin of the hub 120 material can include polyolefin such as polyethylene and polypropylene, polyamide, polycarbonate, and polystyrene.

In accordance with an exemplary embodiment, a hemostatic valve 140 can be attached to a proximal portion 123 of the hub 120 and can help prevent blood from leaking to the outside after flowing into the catheter body 110. The hemostatic valve 140 can include an elastic member having a cross cut 140a, which allows a dilator body 210 to be inserted. In accordance with an exemplary embodiment, the hemostatic valve 140 has a substantially elliptical membrane shape (disk shape) and is fixed in liquid-tight manner to the hub 120 as a result of fitting of a predetermined cap 145.

The hemostatic valve 140 material is not particularly limited. For example, the hemostatic valve 140 material can be silicone rubber, latex rubber, butyl rubber, or isoprene rubber as the elastic member.

In accordance with an exemplary embodiment, the proximal portion 113 of the catheter body 110 can be fixed to an interlock portion 125a of the hub 120. The proximal portion 113 of the catheter body 110 and the interlock portion 125a of the hub 120 can be fixed with an adhesive or the like.

As illustrated in FIG. 2, the strain relief 130 can be externally fitted to the catheter body 110 and the hub 120. The strain relief 130 covers the distal portion 121 of the hub 120 and surrounds the predetermined range of the proximal side of the catheter body 110.

The strain relief 130 material is not particularly limited. Examples of the strain relief 130 material include natural rubber and silicone resin.

As illustrated in FIG. 1, the dilator 200 has the dilator body 210 and a dilator hub 220 that is configured to be connectable to the hub 120. A tube shaped body that can be inserted through the catheter body 110 constitutes the dilator body 210.

In accordance with an exemplary embodiment, the dilator 200 can be used to help prevent breakage of the catheter body 110 or to help expand dermal perforations when the catheter body 110 of the introducer sheath 100 is inserted into the biological lumen R.

Once the dilator body 210 is inserted through the catheter body 110, a distal portion 211 of the dilator body 210 protrudes from the distal portion 111 of the catheter body 110. In accordance with an exemplary embodiment, the distal portion 211 of the dilator body 210 is formed in a tapered shape and tapers toward the distal side of the dilator body 210.

The dilator body 210 material is not particularly limited, and a material similar to those conventionally used can be used as the dilator body 210. Specific examples of the material of the dilator body 210 include polyolefin such as polypropylene (PP) and polyethylene (PE), polyester such as nylon and polyethylene terephthalate (PET), and fluoropolymer such as polyvinylidene fluoride (PVDF) and tetrafluoroethylene-hexafluoropropylene copolymer (FEP).

Although the dilator hub 220 material is not particularly limited, a hard material such as a hard resin is preferable. Specific examples of the dilator hub 220 material in the form of a hard resin can include, for example, polyolefin such as polyethylene and polypropylene, polyamide, polycarbonate, and polystyrene.

The drug part 160 will be described in detail with reference to FIGS. 2 to 4.

In accordance with an exemplary embodiment, the drug part 160 includes a hemostatic agent capable of treating the wound site P in the biological tissue W.

The type of the hemostatic agent is not particularly limited. Examples of the hemostatic agent can include thromboplastin, thrombin, menadione sodium bisulfite, acetomenaphthone, ε-aminocaproic acid, tranexamic acid, sodium carbazochrome sulfonate, and adrenochrome monoaminoguanidine methanesulfonate. For example, a commercially available surgical hemostatic agent such as Matsudyte® manufactured by Sanyo Chemical Industries, Ltd. may be used as the hemostatic agent.

Referring to FIG. 2, the drug part 160 is disposed on the proximal side of the outer surface 117 of the catheter body 110.

In accordance with an exemplary embodiment, by the drug part 160 being disposed on the proximal side of the outer surface 117 of the catheter body 110, the introducer sheath 100 can be percutaneously introduced into the biological lumen R and the desired procedure can be performed without contact between the biological tissue W and the drug part 160. After the desired procedure is completed, the proximal side of the catheter body 110 is inserted into the wound site P. As a result, at least a part of the drug part 160 can be brought into contact with the wound site P (see FIG. 6A). The proximal side of the catheter body 110 is withdrawn from the wound site P with at least a part of the drug part 160 in contact with the wound site P. Then, at least a part of the drug part 160 can be placed at the wound site P (see FIGS. 6B and 7). In accordance with an exemplary embodiment, since the drug part 160 has the hemostatic agent, hemostasis at the wound site P can be promoted by at least a part of the drug part 160 being brought into contact with and placed at the wound site P.

The following method is an example of a method for placing the hemostatic agent at the wound site P during the desired procedure. According to the method, the hemostatic agent is held in the lumen of the tubular member, and the tubular member is inserted into the wound site P in conjunction with an operation for inserting the catheter body 110 into the wound site P or independently of the operation.

With the tubular member inserted in the wound site P, the holding of the hemostatic agent in the tubular member can be released for hemostatic agent placement at the wound site P. The holding of the hemostatic agent in the tubular member can be released by, for example, hemostatic agent extrusion from the lumen of the tubular member.

When the hemostatic agent is placed at the wound site P by means of the tubular member, the wound site P expands as the tubular member as well as the catheter body 110 is inserted into the wound site P. As a result, further bleeding may occur and hemostasis may be hindered. In addition, an operation for releasing the holding of the hemostatic agent in the tubular member can be required for the hemostatic agent to be placed at the wound site P, which results in an increase in procedural complexity during hemostatic agent placement at the wound site P.

With the introducer sheath 100 according to the present embodiment, the wound site P does not have to be excessively expanded during hemostatic agent placement at the wound site P and an operation for releasing the holding of the hemostatic agent in the tubular member described above does not have to be performed. Accordingly, hemostasis at the wound site P can be promoted by means of a relatively simple structure and procedure.

The drug part 160 is disposed in the predetermined range of the catheter body 110 surrounded by the strain relief 130.

As a result, contact between the drug part 160 and another object, the biological tissue W, and the like can be prevented during the desired procedure or transport of the introducer sheath 100. Accordingly, it is possible to prevent peeling of the drug part 160 from the introducer sheath 100 before introduction of the drug part 160 into the wound site P.

Figure 3A:
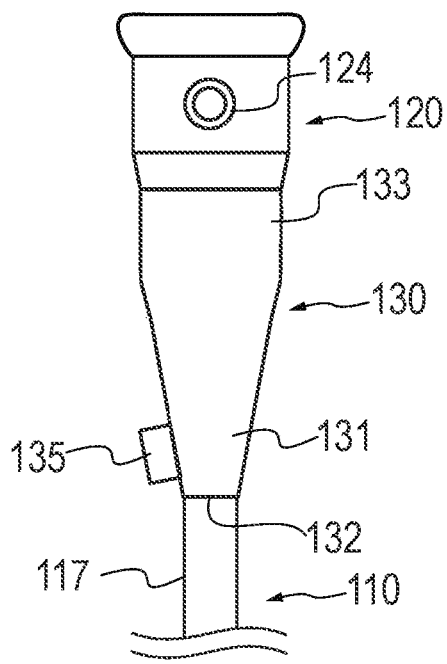
FIG. 3A is an enlarged side view illustrating the vicinity of a strain relief of the introducer sheath according to the first embodiment.
Figure 3B:
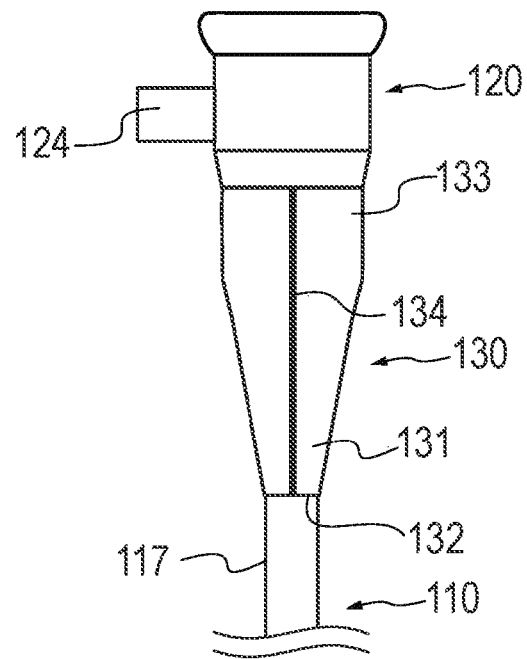
FIG. 3B is an enlarged bottom view illustrating the vicinity of the strain relief of the introducer sheath according to the first embodiment that differs from FIG. 3A.

Referring to FIGS. 3A and 3B, the strain relief 130 is configured to be withdrawable from the outer surface 117 of the catheter body 110.

By withdrawing the strain relief 130 from the outer surface 117 of the catheter body 110, it is possible to relatively easily expose the drug part 160 disposed in the predetermined range of the catheter body 110 surrounded by the strain relief 130. Accordingly, the drug part 160 can be relatively easily introduced into the wound site P.

In accordance with an exemplary embodiment, the strain relief 130 has a slit 134 extending from the proximal side of the catheter body 110 toward the distal side and a grip portion 135 disposed at a position different from the slit 134. The strain relief 130 can be withdrawn from the outer surface 117 of the catheter body 110 by the grip portion 135 being gripped and the strain relief 130 being pulled in a direction away from the catheter body 110.

In accordance with an exemplary embodiment, the slit 134 is continuously formed from the most distal portion 132 of the strain relief 130 to a proximal portion 133. The form of the slit 134 is not particularly limited insofar as the strain relief 130 can be withdrawn from the outer surface 117 of the catheter body 110 by the grip portion 135 being gripped and the strain relief 130 being pulled in a direction away from the catheter body 110. For example, the slit 134 may extend in a portion of the strain relief 130 from the most distal portion 132 of the strain relief 130 toward the proximal portion 133. Alternatively, a plurality of the slits 134 may intermittently extend from the most distal portion 132 of the strain relief 130 toward the proximal portion 133.

When seen in the radial direction of the catheter body 110, in accordance with an exemplary embodiment, the grip portion 135 is disposed on the side that is opposite to the side where the slit 134 is disposed. The grip portion 135 protrudes from the strain relief 130 in a direction away from the outer surface 117 of the catheter body 110 on the distal side of the strain relief 130. The grip portion 135 extends in a direction toward the proximal portion 133 from the most distal portion 132 of the strain relief 130.

Figure 4:
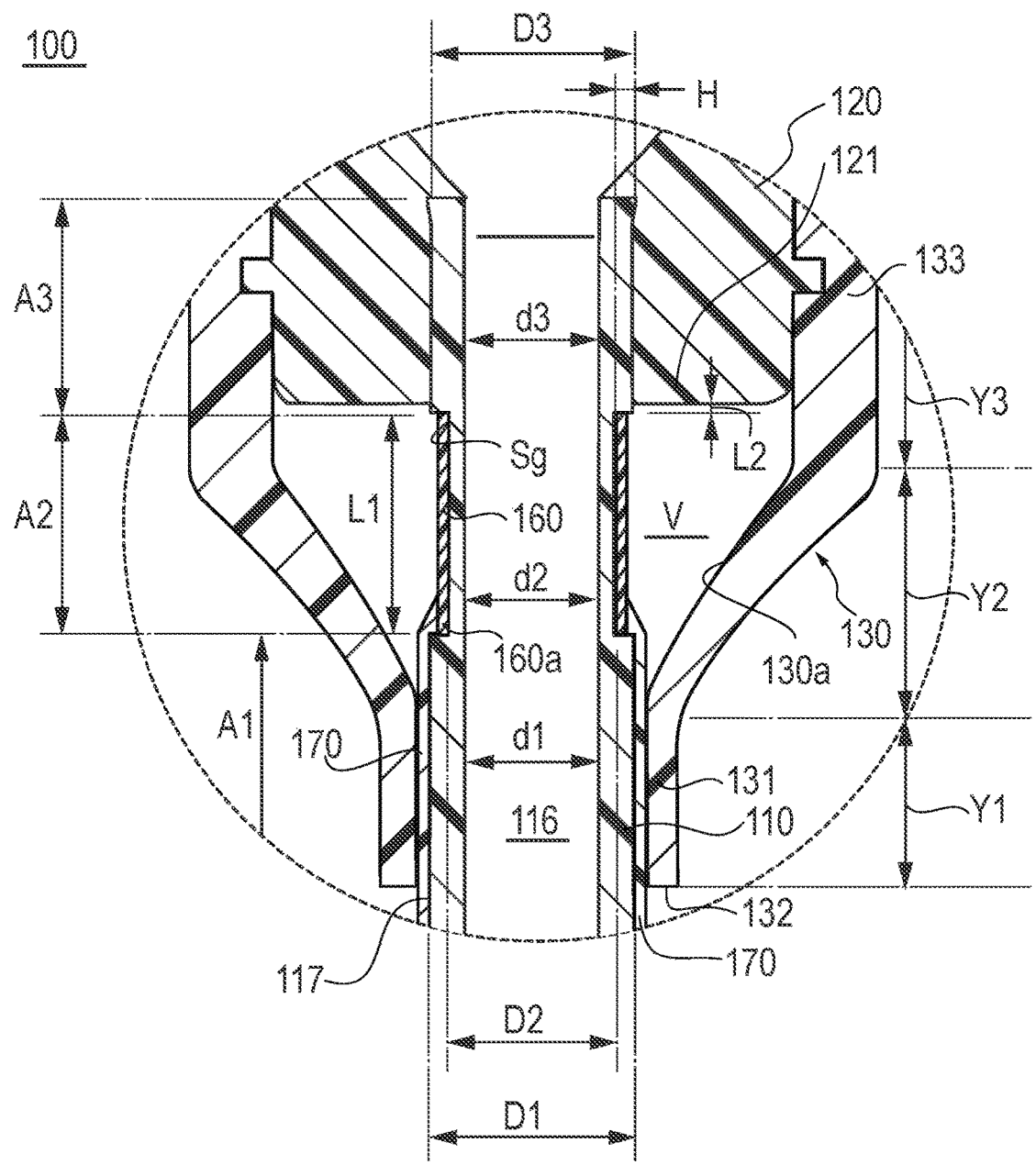
FIG. 4 is an enlarged view illustrating the dashed-line portion IV in FIG. 2.

Referring to FIG. 4, a space portion V is formed between the outer surface 117 of the catheter body 110 and an inner surface 130a of the strain relief 130. In accordance with an exemplary embodiment, the drug part 160 is not in contact with the inner surface 130a of the strain relief 130.

As a result, sticking of the drug part 160 to the strain relief 130 can be avoided, and thus it is possible to prevent the drug part 160 from peeling with the strain relief 130 during withdrawal of the strain relief 130 from the catheter body 110.

The shape of the strain relief 130 is not particularly limited insofar as the space portion V is formed between the outer surface 117 of the catheter body 110 and the inner surface 130a of the strain relief 130 and the drug part 160 is not in contact with the inner surface 130a of the strain relief 130. In the present embodiment, the strain relief 130 is provided with a distal region Y1, an intermediate region Y2, and a proximal region Y3. The intermediate region Y2 is connected to the distal region Y1, is disposed closer to the proximal side of the catheter body 110 than the distal region Y1 (i.e., the intermediate region Y2 is proximal to the distal region Y1), and extends at an angle in a direction away from the outer surface 117 of the catheter body 110. The proximal region Y3 is connected to the intermediate region Y2 and is disposed closer to the proximal side than the intermediate region Y2 (i.e., the proximal region Y3 is proximal to the intermediate region Y2).

Referring to FIGS. 2 and 4, the catheter body 110 has a first region A1 and a second region A2 disposed closer to the proximal side than the first region A1 (i.e., the second region A2 is proximal to the first region A1). The second region A2 has an outer diameter D2, which is smaller than an outer diameter D1 of the first region A1. The second region A2 is provided closer to the proximal side of the catheter body 110 than a most distal portion 132 of the strain relief 130 (i.e., the second region A2 is proximal to a most distal portion 132 of the strain relief 130). The drug part 160 is disposed in the second region A2. Note that, a medical device such as a catheter is inserted into the lumen 116 of the catheter body 110, and thus it is preferable that an inner diameter d1 of the first region A1 and an inner diameter d2 of the second region A2 are equal to each other.

During introduction of the drug part 160 into the wound site P, resistance from the biological tissue W can act on a distal portion 160a, which first comes into contact with the biological tissue W in the drug part 160. In accordance with an exemplary embodiment, the drug part 160 is disposed in the second region A2 and the outer diameter D2 of the second region A2 is smaller than the outer diameter D1 of the first region A1. Accordingly, during introduction of the drug part 160 into the wound site P, the biological tissue W is unlikely to come into contact with the distal portion 160a of the drug part 160 and the resistance that acts on the distal portion 160a from the biological tissue W can be reduced. Accordingly, it is possible to prevent peeling of the drug part 160 from the introducer sheath 100 during introduction of the drug part 160 into the wound site P.

In accordance with an exemplary embodiment, the rigidity of an introducer sheath having a strain relief can significantly change in the boundary portion between a catheter body and the strain relief. Accordingly, when the catheter body is bent, the catheter body may kink in the vicinity of the most distal portion of the strain relief.

In the introducer sheath 100 according to the present embodiment, the second region A2 having the outer diameter D2 smaller than the outer diameter D1 of the first region A1 is disposed closer to the proximal side than the most distal portion 132 of the strain relief 130 (i.e., the second region A2 is proximal to the most distal portion 132 of the strain relief 130). Accordingly, the introducer sheath 100 has sufficient kink resistance (i.e., ability to prevent kinking) even when the second region A2 having the drug part 160 is provided.

The catheter body 110 has a third region A3 disposed closer to the proximal side than the second region A2 (i.e., the third region A2 is proximal to the second region A2). The third region A3 has an outer diameter D3, which exceeds (i.e., greater than) the outer diameter D2 of the second region A2. The second region A2 is a groove portion Sg recessed toward the inner space of the catheter body 110. Note that, a medical device such as a catheter can be inserted into the lumen 116 of the catheter body 110, and thus it is preferable that the inner diameter d1 of the first region A1, the inner diameter d2 of the second region A2, and an inner diameter d3 of the third region A3 are equal to one another.

In accordance with an exemplary embodiment, since the second region A2 where the drug part 160 is disposed is the groove portion Sg, the boundary between the region (second region A2) where the drug part 160 is disposed on the outer surface 117 of the catheter body 110 and the regions (first and third regions A1 and A3) where the drug part 160 is not disposed on the outer surface 117 of the catheter body 110 becomes clearer (i.e., relatively easy to perceive). Accordingly, the range where the drug part 160 is disposed on the outer surface 117 of the catheter body 110 can be more clearly grasped, and thus the drug part 160 can be brought into contact with and placed at the wound site P in a more reliable manner.

In accordance with an exemplary embodiment, the groove portion Sg can be provided over an entire circumference of the outer surface 117 of the catheter body 110 in the range that is closer to the proximal side of the catheter body 110 than the most distal portion 132 of the strain relief 130 and closer to the distal side than the distal portion 121 of the hub 120.

As a result, the drug part 160 can be disposed over the entire circumference of the catheter body 110. Accordingly, during introduction of the drug part 160 into the wound site P, the contact area of the drug part 160 with respect to the wound site P can be increased.

In accordance with an exemplary embodiment, the thickness of the drug part 160 is not particularly limited, and the thickness can be set within a range of, for example, 0.01 mm to 0.15 mm. In accordance with an exemplary embodiment, a depth H of the groove portion Sg exceeds the thickness of the drug part 160. The depth H of the groove portion Sg can be set within a range of, for example, 0.01 mm to 0.20 mm.

In accordance with an exemplary embodiment, a width L1 of the groove portion Sg is not particularly limited, and the width L1 can be set within a range of, for example, 5 mm to 30 mm. A distance L2 from the distal portion 121 of the hub 120 to the groove portion Sg is not particularly limited, and the distance L2 can be set within a range of, for example, 0 mm to 70 mm.

In accordance with an exemplary embodiment, a part of the hydrophilic lubricating layer 170 covers the distal portion 160a of the drug part 160.

As a result of the hydrophilic lubricating layer 170, the resistance that acts on the distal portion 160a of the drug part 160 from the biological tissue W can be suppressed during introduction of the drug part 160 into the wound site P. Accordingly, it is possible to prevent peeling of the drug part 160 from the introducer sheath 100 during introduction of the drug part 160 into the wound site P.

The drug part 160 has a drug carrier carrying the hemostatic agent. In accordance with an exemplary embodiment, the drug carrier is a biodegradable material that softens at a body temperature. As a result, the drug part 160 softens when the drug part 160 is brought into contact with the wound site P, and thus at least a part of the drug part 160 can be placed at the wound site P in a relatively reliable manner.

The type of the biodegradable material that constitutes the drug carrier is not particularly limited, and gelatin can be used as an example.

Next, a treatment method using the introducer assembly 10 according to the present embodiment will be described.

The treatment method using the introducer assembly 10 according to the present embodiment includes a step of placing the introducer sheath 100, a step of performing the desired procedure, a step of introducing the drug part 160 into the wound site P, and a step of placing at least a part of the drug part 160 at the wound site P.

Referring to FIGS. 5A to 5F, in the step of placing the introducer sheath 100, the biological lumen R where the introducer sheath 100 is to be placed is punctured with an introduction needle 50 (see FIG. 5A) and a guide wire 60 is inserted into the biological lumen R through a lumen 50a of the introduction needle 50 (see FIG. 5B). Then, with the guide wire 60 placed in the biological lumen R, the introduction needle 50 is withdrawn from the biological lumen R and the guide wire 60 is placed in the biological lumen R (see FIG. 5C). Subsequently, puncturing with the introducer assembly 10 is performed with the dilator 200 directed along the guide wire 60 placed in the biological lumen R (see FIGS. 5D and 5E) and the guide wire 60 and the dilator 200 are withdrawn from the introducer sheath 100 with the introducer sheath 100 placed in the biological lumen R.

In the step of performing the desired procedure, a treatment instrument such as a catheter and a guide wire is introduced into the biological lumen R through the hemostatic valve 140 of the introducer sheath 100 with the introducer sheath 100 placed in the biological lumen R. Then, the procedure such as percutaneous coronary intervention (PTCA) is performed. Once the procedure is completed, the treatment instrument introduced into the biological lumen R is withdrawn from the inside of the biological lumen R.

Referring to FIG. 6A, in the step of introducing the drug part 160 into the wound site P, the drug part 160 is exposed, the proximal side of the introducer sheath 100 is moved toward the wound site P, the drug part 160 is introduced into the wound site P, and at least a part of the drug part 160 is brought into contact with the wound site P.

During the exposure of the drug part 160, the grip portion 135 of the strain relief 130 is gripped and the grip portion 135 is pulled in a direction away from the catheter body 110. As a result, the catheter body 110 passes through the slit 134 of the strain relief 130 and the strain relief 130 is withdrawn from the catheter body 110.

When the proximal side of the introducer sheath 100 is moved toward the wound site P, the guide wire 60 and the dilator 200 are inserted through the hemostatic valve 140 of the introducer sheath 100, and the introducer sheath 100 is moved in a state where the guide wire 60 and the dilator 200 are inserted in the lumen of the introducer sheath 100.

In accordance with an exemplary embodiment, the drug part 160 may be exposed either before or after the insertion of the guide wire 60 and the dilator 200 through the hemostatic valve 140 of the introducer sheath 100.

Referring to FIG. 6B, in the step of placing at least a part of the drug part 160 at the wound site P, at least a part of the drug part 160 is placed at the wound site P by the introducer sheath 100 being withdrawn from the biological lumen R in a state where at least a part of the drug part 160 is in contact with the wound site P. Since the drug part 160 has the hemostatic agent, hemostasis at the wound site P can be promoted by at least a part of the drug part 160 being brought into contact with and placed at the wound site P.

In the step of placing at least a part of the drug part 160 at the wound site P, at least a part of the drug part 160 is placed at the site of the wound site P that is close to the biological lumen R. Hemostasis at the wound site P can be more effectively promoted by this method than by, for example, dermal application of a hemostatic agent-containing sheet material. The withdrawal of the introducer sheath 100 from the biological lumen R is performed while the wound site P is compressed. As a result, the wound site P can be pressed against the drug part 160 when the introducer sheath 100 is withdrawn from the biological lumen R. Accordingly, the drug part 160 can be rubbed against and scraped off at the wound site P in conjunction with the withdrawal operation for the introducer sheath 100.

As a result, at least a part of the drug part 160 can be relatively efficiently placed at the wound site P.

When the introducer sheath 100 is withdrawn from the biological lumen R, bleeding at the wound site P is somewhat stopped by the hemostatic agent of the drug part 160. Accordingly, hemostatic state maintenance after the withdrawal of the introducer sheath 100 can be performed, for example, with a bandage or the like.

In accordance with an exemplary embodiment, with the introducer sheath 100 according to the present embodiment, bleeding at the wound site P can be stopped in a relatively short time by means of a bandage or the like after the introducer sheath 100 is withdrawn from the biological lumen R. Accordingly, the time required for hemostasis at the wound site P can be shortened and the physical burden on a patient lessened or reduced. By shortening the time required for hemostasis at the wound site P, it is possible to suppress the occurrence of numbness and pain that is attributable to nerve compression. In addition to lessening or reducing a patient's physical burden, the introducer catheter 100 and methods as disclosed herein can also be useful in the following points.

For example, in stopping bleeding by compressing the wound site P, a health care worker such as a doctor and a nurse usually performs a depressurizing operation in order to prevent the numbness and pain described above. During the depressurizing operation, the internal pressure of a balloon or the like that compresses the wound site P is gradually lowered at a predetermined time interval (for example, every hour). The depressurizing work can be burdensome on the health care worker's part. The introducer sheath according to the present embodiment is capable of lessening the depressurizing work, and thus can be useful in lessening health care workers' burden as well.

In accordance with an exemplary embodiment, the introducer sheath 100 according to the present embodiment is provided with the drug part 160 having the hemostatic agent capable of treating the wound site P in the biological tissue W. The drug part 160 is disposed on the proximal side of the outer surface 117 of the catheter body 110. By the drug part 160 being disposed on the proximal side of the outer surface 117 of the catheter body 110, the introducer sheath 100 can be percutaneously introduced into the biological lumen R and the desired procedure can be performed without contact between the biological tissue W and the drug part 160. After the desired procedure is completed, the proximal side of the catheter body 110 is inserted into the wound site P. As a result, at least a part of the drug part 160 can be brought into contact with the wound site P. The proximal side of the catheter body 110 is withdrawn from the wound site P with at least a part of the drug part 160 in contact with the wound site P. Then, at least a part of the drug part 160 can be placed at the wound site P. Since the drug part 160 has the hemostatic agent, hemostasis at the wound site P can be promoted by at least a part of the drug part 160 being brought into contact with and placed at the wound site P. Accordingly, after withdrawal of the introducer sheath percutaneously introduced into a biological lumen, the time required for hemostasis at the wound site can be shortened and the physical burden on the patient can be lessened or reduced as a result.

In accordance with an exemplary embodiment, the introducer sheath 100 according to the present embodiment further includes the strain relief 130 covering the distal portion 121 of the hub 120 and surrounding the predetermined range of the proximal side of the catheter body 110. The drug part 160 is disposed in the predetermined range of the catheter body 110 surrounded by the strain relief 130. As a result, contact between the drug part 160 and another object, the biological tissue W, and the like can be prevented during the desired procedure or transport of the introducer sheath 100. Accordingly, it is possible to prevent peeling of the drug part 160 from the introducer sheath 100 before introduction of the drug part 160 into the wound site P. Accordingly, the time required for hemostasis at the wound site P by means of the introducer sheath 100 can be shortened in a reliable manner.

In the introducer sheath 100 according to the present embodiment, the catheter body 110 has the first region A1 and the second region A2 disposed closer to the proximal side than the first region A1 (i.e., the first region A1 is proximal to the second region A2). The second region A2 has the outer diameter D2, which is smaller than the outer diameter D1 of the first region A1. The drug part 160 is disposed in the second region A2. During introduction of the drug part 160 into the wound site P, the resistance from the biological tissue W greatly acts on the distal portion 160*a*, which first comes into contact with the biological tissue W in the drug part 160. The drug part 160 is disposed in the second region A2 and the outer diameter D2 of the second region A2 is smaller than the outer diameter D1 of the first region A1. Accordingly, during introduction of the drug part 160 into the wound site P, the biological tissue W is unlikely to come into contact with the distal portion 160*a* of the drug part 160 and the resistance that acts on the distal portion 160*a* of the drug part 160 from the biological tissue W can be reduced. Accordingly, it is possible to prevent peeling of the drug part 160 from the introducer sheath 100 during introduction of the drug part 160 into the wound site P. In addition, the drug part 160 can be placed at the wound site P in a more reliable manner, and thus the time required for hemostasis at the wound site P by means of the introducer sheath 100 can be shortened in a reliable manner.

In the introducer sheath 100 according to the present embodiment, the catheter body 110 has the third region A3 disposed closer to the proximal side than the second region A2 (i.e., the third region A3 is proximal to the second region A2). The third region A3 has the outer diameter D3, which exceeds (i.e., greater than) the outer diameter D2 of the second region A2. The drug part 160 is disposed in the second region A2. The second region A2 is the groove portion Sg recessed toward the inner space of the catheter body 110. Since the second region A2 where the drug part 160 is disposed is the groove portion Sg, the boundary between the region (second region A2) where the drug part 160 is disposed on the outer surface 117 of the catheter body 110 and the regions (first and third regions A1 and A3) where the drug part 160 is not disposed on the outer surface 117 of the catheter body 110 becomes clearer (i.e., relatively easy to perceive). Accordingly, the range where the drug part 160 is disposed on the outer surface 117 of the catheter body 110 can be more clearly grasped, and thus the drug part 160 can be brought into contact with and placed at the wound site P in a more reliable manner. Accordingly, the time required for hemostasis at the wound site P by means of the introducer sheath 100 can be shortened in a reliable manner.

In the introducer sheath 100 according to the present embodiment, the groove portion Sg is provided over the entire circumference of the outer surface 117 of the catheter body 110 in the range that is closer to the proximal side of the catheter body 110 than the most distal portion 132 of the strain relief 130 and closer to the distal side of the catheter body 110 than the distal portion 121 of the hub 120. As a result, the drug part 160 can be disposed over the entire circumference of the catheter body 110. Accordingly, during introduction of the drug part 160 into the wound site P, the contact area of the drug part 160 with respect to the wound site P can be increased. Accordingly, the time required for hemostasis at the wound site P by means of the introducer sheath 100 can be shortened in a reliable manner.

In accordance with an exemplary embodiment, in the introducer sheath 100 according to the present embodiment, the hydrophilic lubricating layer 170 for providing surface lubricity during wetting is disposed on the outer surface 117 of the catheter body 110. At least a part of the hydrophilic lubricating layer 170 covers the distal portion 160a of the drug part 160. During introduction of the drug part 160 into the wound site P, the resistance from the biological tissue W acts on the distal portion 160a, which first comes into contact with the biological tissue W in the drug part 160. Since at least a part of the hydrophilic lubricating layer 170 covers the distal portion 160a of the drug part 160, the resistance that acts on the distal portion 160a of the drug part 160 from the biological tissue W can be suppressed during introduction of the drug part 160 into the wound site P. Accordingly, it is possible to prevent peeling of the drug part 160 from the introducer sheath 100 during introduction of the drug part 160 into the wound site P. In addition, the time required for hemostasis at the wound site P by means of the introducer sheath 100 can be shortened in a reliable manner.

In accordance with an exemplary embodiment, in the introducer sheath 100 according to the present embodiment, the drug part 160 has the drug carrier carrying the hemostatic agent as well. The drug carrier is a biodegradable material that softens at a body temperature. As a result, the drug part 160 is softened by the body temperature after the drug part 160 comes into contact with the wound site P. Accordingly, the drug part 160 is not softened by the body temperature when introduced into the wound site P, and thus the drug part 160 passes through the dermal wound site P in a relatively hard state. As a result, the drug part 160 can be prevented from falling off the skin. Since the drug part 160 softens at the body temperature after coming into contact with the wound site P, at least a part of the drug part 160 can be placed at the wound site P in a reliable manner. Accordingly, the time required for hemostasis at the wound site P by means of the introducer sheath 100 can be shortened in a reliable manner.

Second Embodiment

In the introducer assembly 10 according to the first embodiment described above, the drug part 160 is disposed in the predetermined range of the catheter body 110 surrounded by the strain relief 130. In accordance with an exemplary embodiment, an introducer assembly 20 according to the present embodiment differs from the introducer assembly 10 according to the first embodiment described above in that a drug part 360 is disposed on the proximal side of the outer surface 117 of a catheter body 310 and outside of a strain relief 330.

In accordance with an exemplary embodiment, the introducer assembly 10 has an introducer sheath 300 and the dilator 200. The configuration of the dilator 200 is the same as that of the first embodiment described above, and thus the configuration of the dilator 200 will not be described below.

Figure 8:
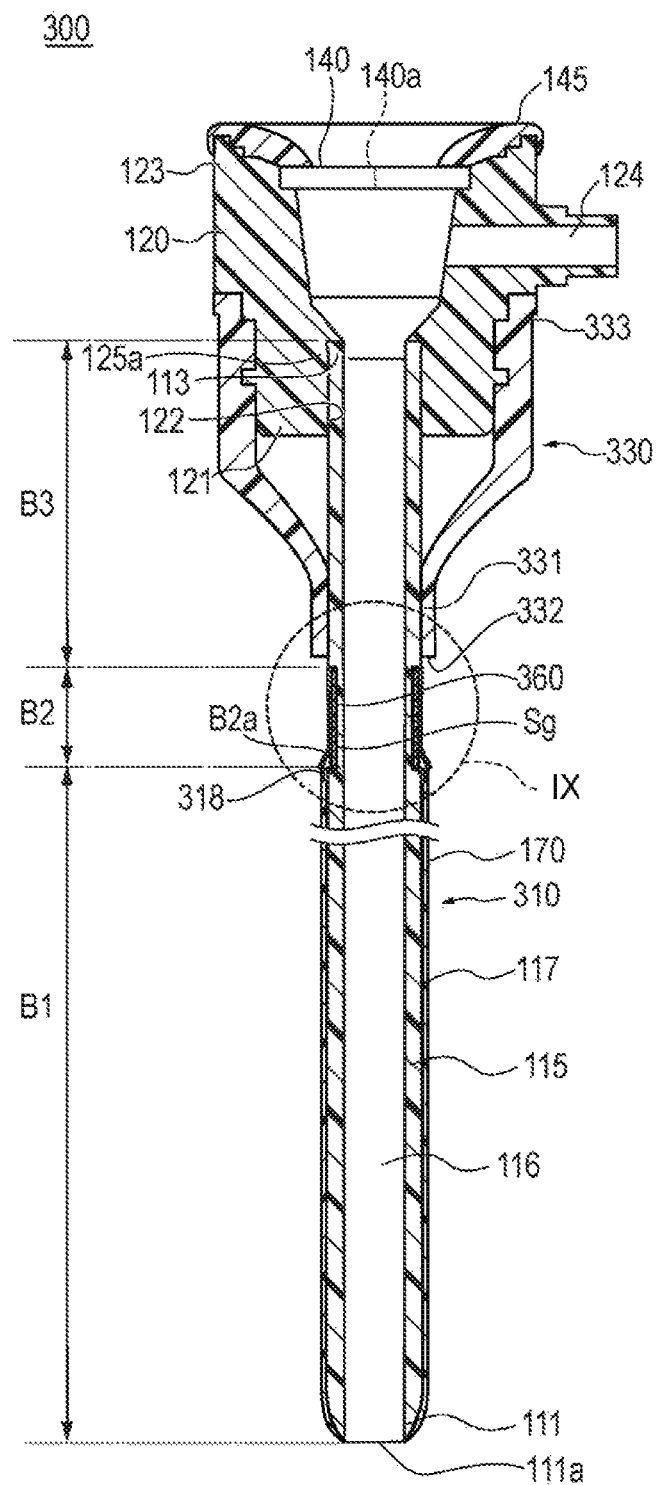
FIG. 8 is a cross-sectional view illustrating an introducer sheath according to a second embodiment.
Figure 9:
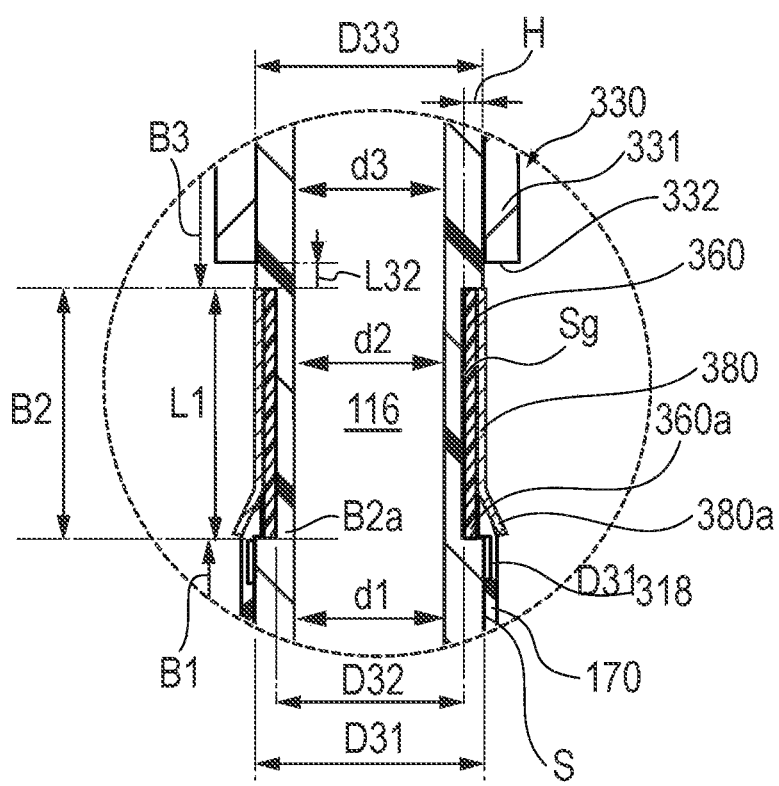
FIG. 9 is an enlarged view illustrating the dashed-line portion IX in FIG. 8.

Referring to FIGS. 8 and 9, the introducer sheath 300 according to the present embodiment includes the catheter body 310 to be percutaneously introduced into the biological lumen R, the hub 120 connected to the proximal side of the catheter body 310, the drug part 360 having a hemostatic agent capable of treating the wound site P in the biological tissue W, and the strain relief 330 covering the distal portion 121 of the hub 120 and surrounding a predetermined range of the proximal side of the catheter body 310. The catheter body 310 has a first region B1 and a second region B2 disposed closer to the proximal side than the first region B1 (i.e., the first region B1 is proximal to the second region B2). The second region B2 has an outer diameter D32, which is smaller than an outer diameter D31 of the first region B1. A distal end B2a of the second region B2 is located closer to the distal side than the most distal portion 332 of the strain relief 330, and the drug part 360 is disposed in the second region B2. The introducer sheath 300 according to the present embodiment further includes a cover member 380 covering the drug part 360.

The introducer sheath 300 according to the present embodiment will be described below. Note that, the same configurations as those of the introducer sheath 100 according to the first embodiment described above are denoted by the same reference numerals, and the description of the configurations as those of the introducer sheath 100 according to the first embodiment is omitted.

The configuration of the strain relief 330 is the same as the configuration of the strain relief 130 according to the first embodiment described above except that the strain relief 330 is not configured to be withdrawable. Specifically, the strain relief 330 has the same configuration as the strain relief 130 according to the first embodiment described above except that the strain relief 330 does not have the slit 134 and the grip portion 135.

The distal end B2a of the second region B2 is located closer to the distal side than the most distal portion 332 of the strain relief 330, and the drug part 360 is disposed in the second region B2. In accordance with an exemplary embodiment, the drug part 360 is disposed on the proximal side of the outer surface 117 of the catheter body 310 and outside the strain relief 330.

As a result, the drug part 360 can be introduced into the wound site P without withdrawal of the strain relief 330, and thus hemostasis at the wound site P can be promoted or induced rather quickly. Since the strain relief 330 does not have to be configured to be withdrawable, the structure of the introducer sheath 300 becomes relatively simpler and manufacturing of the introducer sheath 300 is also relatively simpler.

The catheter body 310 has a third region B3 disposed closer to the proximal side than the second region B2 (i.e., the third region B3 is proximal to the second region B2). The third region B3 has an outer diameter D33, which exceeds (i.e., greater than) the outer diameter D32 of the second region B2. The second region B2 is the groove portion Sg recessed toward the lumen 116 of the catheter body 310. The third region B3 is located closer to the distal side than the most distal portion 332 of the strain relief 330.

The thickness of the drug part 360 can be set as in the case of the drug part 160 according to the first embodiment described above. The depth H of the groove portion Sg exceeds (i.e., greater than) the thickness of the drug part 360. The depth H of the groove portion Sg can be set as in the case of the drug part 160 according to the first embodiment described above.

The width L1 of the groove portion Sg can be set as in the case of the drug part 160 according to the first embodiment described above. A distance L32 from the most distal portion 332 of the strain relief 330 to the groove portion Sg is not particularly limited, and the distance L32 can be set within a range of, for example, 0 mm to 10 mm.

The cover member 380 covers the drug part 360. As a result, contact between the drug part 360 and another object, the biological tissue W, and the like can be prevented during the desired procedure or transport of the introducer sheath 300. Accordingly, it is possible to prevent peeling of the drug part 360 from the introducer sheath 300 before introduction of the drug part 360 into the wound site P.

A distal portion 380a of the cover member 380 is removably fixed to the outer surface 117 of the catheter body 310. As a result, it is possible to remove the cover member 380 from the drug part 360 by gripping the distal portion 380a of the cover member 380 and expose the drug part 360 from the cover member 380.

Although the cover member 380 has a tube shape, the shape of the cover member 380 is not limited to the tube shape insofar as the cover member 380 is capable of covering the drug part 360. The cover member 380 material is not particularly limited, and a resinous film or the like can be used as the material for the cover member 380.

The catheter body 310 has a marker portion 318 with which a distal portion 360a of the drug part 360 can be visually observed. As a result, the place where the drug part 360 is disposed on the outer surface 117 of the catheter body 310 can be more clearly grasped, and thus the drug part 360 can be brought into contact with and placed at the wound site P in a relatively reliable manner.

In accordance with an exemplary embodiment, the marker portion 318 has a color different from the color of the catheter body 310 and has a band shape having a constant width along the circumferential direction of the catheter body 310. The color of the marker portion 318 is not particularly limited. The color can be, for example, white. The width of the marker portion 318 is not particularly limited. The width can be set within a range of, for example, 5 mm to 30 mm.

In accordance with an exemplary embodiment, the color of the drug part 360 is different from the color of the catheter body 310. As a result, it is possible to rather easily grasp the range where the drug part 360 is disposed on the outer surface 117 of the catheter body 310. Accordingly, the drug part 360 can be introduced into the wound site P in a relatively reliable manner. It is possible to rather easily determine whether or not the drug part 360 is disposed on the outer surface 117 of the catheter body 310, and thus it is possible to reduce the risk of erroneous use of the introducer sheath 300 where the drug part 360 is not disposed.

In accordance with an exemplary embodiment, the color of the drug part 360 is not particularly limited. The color of the drug part 360 can be, for example, white. Methods for coloring the drug part 360 are not particularly limited. The drug part 360 can be colored, for example, by being mixed with a known coloring material.

In accordance with an exemplary embodiment, the treatment method using the introducer assembly 20 according to the present embodiment includes a step of placing the introducer sheath 300, a step of performing the desired procedure, a step of introducing the drug part 360 into the wound site P, and a step of placing at least a part of the drug part 360 at the wound site P. The treatment method is identical to the treatment method according to the first embodiment described above except for the step of introducing the drug part 360 into the wound site P, and thus the identical steps will not be described below.

The step of introducing the drug part 360 into the wound site P is identical to the step of introducing the drug part 160 into the wound site P in the treatment method according to the first embodiment described above except for a procedure for exposing the drug part 360.

During the exposure of the drug part 360, the distal portion 380a of the cover member 380 is gripped and the cover member 380 is pulled in a direction away from the catheter body 310. Then, the cover member 380 is removed from the catheter body 310 and the drug part 360 is exposed.

In the introducer sheath 300 according to the present embodiment, the catheter body 310 has the first region B1 and the second region B2 disposed closer to the proximal side than the first region B1 (i.e., the first region B1 is proximal to the second region B2). The second region B2 has the outer diameter D32, which is smaller than the outer diameter D31 of the first region B1. The distal end B2a of the second region B2 is located closer to the distal side of the catheter body 310 than the most distal portion 132 of the strain relief 330, and the drug part 360 is disposed in the second region B2. As a result, the drug part 360 can be brought into contact with and placed at the wound site P without withdrawal of the strain relief 330. Accordingly, the time required for hemostasis at the wound site P by means of the introducer sheath 300 can be rather quickly shortened.

In the introducer sheath 300 according to the present embodiment, the catheter body 310 has the third region B3 disposed closer to the proximal side than the second region B2 (i.e., the third region B3 is proximal to the second region B2). The third region B3 has the outer diameter D33, which exceeds (i.e., greater than) the outer diameter D32 of the second region B2. The drug part 360 is disposed in the second region B2, and the second region B2 is the groove portion Sg recessed toward the lumen 116 of the catheter body 310. The third region B3 is located closer to the distal side than the most distal portion 132 of the strain relief 330. As a result, the boundary between the region (second region B2) where the drug part 360 is disposed on the outer surface 117 of the catheter body 310 and the regions (first and third regions B1 and B3) where the drug part 360 is not disposed on the outer surface 117 of the catheter body 310 becomes clearer (i.e., relatively easy to perceive). Accordingly, the range where the drug part 360 is disposed on the outer surface 117 of the catheter body 310 can be clearly grasped, and thus the drug part 360 can be brought into contact with and placed at the wound site P in a relatively reliable manner. Accordingly, the time required for hemostasis at the wound site P by means of the introducer sheath 300 can be shortened in a rather reliable manner.

In the introducer sheath 300 according to the present embodiment, the catheter body 310 has the marker portion 318 with which the distal portion 360a of the drug part 360 can be visually observed. As a result of the user of the marker portion 318, the place where the drug part 360 is disposed on the outer surface 117 of the catheter body 310 can be clearly grasped, and thus the drug part 360 can be brought into contact with and placed at the wound site P in a more reliable manner. Accordingly, the time required for hemostasis at the wound site P by means of the introducer sheath 300 can be shortened in a rather reliable manner.

Modification Example

In the second embodiment described above, the hub 120 and the strain relief 330 are configured as separate bodies. Alternatively, the hub 120 and the strain relief 330 may be integrally configured as a single unit.

Figure 10:
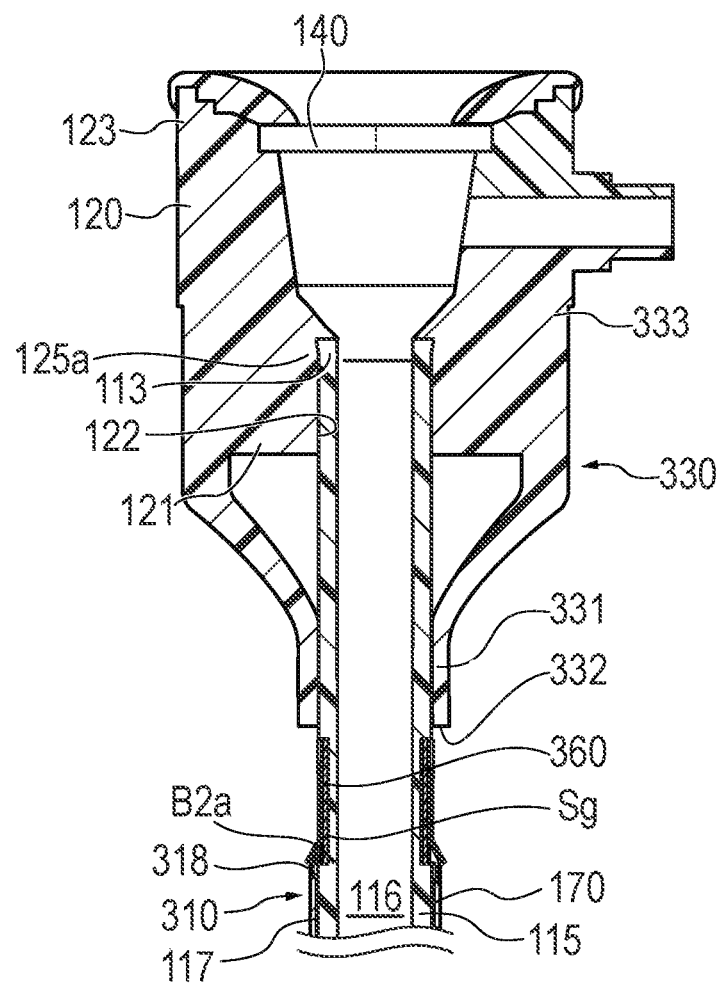
FIG. 10 is a cross-sectional view of the proximal side of an introducer sheath according to a modification example.

FIG. 10 is a cross-sectional view of the proximal side of the introducer sheath according to the present modification example.

As illustrated in FIG. 10, the hub 120 and the strain relief 330 are integrally configured in the introducer sheath according to the present modification example. Specifically, the strain relief 330 extends from the distal portion 121 of the hub 120, extends while decreasing in diameter toward the distal side of the catheter body 310, and surrounds a predetermined range of the proximal side of the catheter body 310.

In accordance with an exemplary embodiment, the hub 120 and the strain relief 330 can be made of the same material. The hub 120 material and the strain relief 330 material can be the same as the material described above as the material that constitutes the hub 120 in the first embodiment. In accordance with an exemplary embodiment, the hub 120 and the strain relief 330 can be formed by integral molding using injection molding or the like.

The introducer sheath according to the present modification example achieves the following action and effect in addition to the action and effect of the introducer sheath 300 according to the second embodiment described above.

Since the hub 120 and the strain relief 330 are integrally configured, the number of parts can be reduced as compared with a case where the hub 120 and the strain relief 330 are configured as separate bodies. A process for assembling the hub 120 and the strain relief 330 can be reduced, and thus manufacturing productivity improvement can be achieved. As a result, with the introducer sheath according to the present modification example, the introducer sheath capable of lessening a patient's physical burden can be provided at a relatively low cost.

Although the introducer sheath according to the disclosure has been described above based on the first embodiment, the second embodiment, and the modification example, the disclosure is not limited to the configurations described above. The present disclosure can be appropriately changed based on the description of the claims.

For example, the drug part 160 is completely covered with the strain relief 130 in the first embodiment described above and the drug part 360 is completely exposed from the strain relief 330 in the second embodiment described above. Alternatively, a part of the drug part may be covered with the strain relief and the other part of the drug part may be exposed from the strain relief. With the above-described configuration, hemostasis at the wound site P can be promoted and the time required for the hemostasis can be shortened as in the case of the first and second embodiments described above.

In the case of the configuration in which a part of the drug part is covered with the strain relief and the other part of the drug part is exposed from the strain relief, a part of the drug part is interposed between the distal portion of the strain relief and the catheter body 110. Accordingly, a part of the drug part is likely to come into contact with the distal portion of the strain relief. Conceivable in order to avoid the contact is a method for providing a clearance between the distal portion of the strain relief and the outer surface 117 of the catheter body 110. However, it is difficult for the strain relief to follow the movement of the site on the proximal side of the catheter body 110, and thus it may be impossible to effectively exhibit an original function of the strain relief for hindering bending of the catheter body 110. According to the first and second embodiments described above, such a problem does not arise, and thus the first and second embodiments described above can be more preferable.

In the first and second embodiments described above, at least a part of the hydrophilic lubricating layer 170 covers the distal portion of the drug part. In an alternative configuration, at least a part of the hydrophilic lubricating layer may surround the entire drug part.

In the first embodiment described above, the strain relief 130 is configured to be withdrawable from the outer surface 117 of the catheter body 110. The disclosure is not particularly limited insofar as the drug part 160 covered with the strain relief 130 can be exposed. In an alternative exemplary configuration, the distal portion of the strain relief may be allowed to be turned up toward the proximal side of the catheter body.

Although the introducer sheath according to the first embodiment, the second embodiment, and the modification example has the strain relief, the disclosure is not limited to the form that has the strain relief and the disclosure can be implemented in a form that lacks a strain relief as well.

The same action and effect as those of the introducer sheath according to the first and second embodiments can be obtained even without a strain relief.

The detailed description above describes embodiments of an introducer sheath used for an introducer assembly as a medical instrument. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An introducer sheath comprising:
   a catheter body configured to be percutaneously introduced into a biological lumen;
   a hub configured to be connected to a proximal side of the catheter body;
   a drug part having a hemostatic agent capable of treating a wound site in biological tissue, and wherein the drug part is disposed on a proximal side of an outer surface of the catheter body; and
   a strain relief covering a distal portion of the hub and surrounding a predetermined range of the proximal side of the catheter body, and wherein the drug part is disposed in the predetermined range of the catheter body surrounded by the strain relief.

2. The introducer sheath according to claim 1, wherein the catheter body has a first region and a second region, the second region being proximal to the first region and having an outer diameter smaller than an outer diameter of the first region;
the second region being proximal to a most distal portion of the strain relief; and
wherein the drug part is disposed in the second region.

3. The introducer sheath according to claim 2, wherein the catheter body has a third region, the third region being proximal to the second region and having an outer diameter exceeding the outer diameter of the second region, and the second region having a groove portion recessed toward an inner space of the catheter body.

4. The introducer sheath according to claim 3, wherein the groove portion is provided over the entire circumference of the outer surface of the catheter body in a range closer to the proximal side of the catheter body than the most distal portion of the strain relief and closer to a distal side of the catheter body than the distal portion of the hub.

5. An introducer sheath comprising:
a catheter body configured to be percutaneously introduced into a biological lumen;
a hub configured to be connected to a proximal side of the catheter body;
a drug part having a hemostatic agent capable of treating a wound site in biological tissue, and wherein the drug part is disposed on a proximal side of an outer surface of the catheter body;
a strain relief covering a distal portion of the hub and surrounding a predetermined range of the proximal side of the catheter body, and wherein the catheter body has a first region and a second region, the second region being proximal to the first region and having an outer diameter smaller than an outer diameter of the first region;
a distal end of the second region is located closer to a distal side of the catheter body than a most distal portion of the strain relief; and
wherein the drug part is disposed in the second region.

6. The introducer sheath according to claim 5, wherein the catheter body has a third region, the third region being proximal to the second region and having an outer diameter exceeding an outer diameter of the second region;
the second region being a groove portion recessed toward a lumen of the catheter body; and
wherein the third region is located closer to the distal side of the catheter body than the most distal portion of the strain relief.

7. The introducer sheath according to claim 5, wherein the catheter body has a marker portion with which a distal portion of the drug part can be visually observed.

8. The introducer sheath according to claim 1, further comprising:
a hydrophilic lubricating layer for providing surface lubricity during wetting is disposed on the outer surface of the catheter body; and
at least a part of the hydrophilic lubricating layer covers a distal portion of the drug part.

9. The introducer sheath according to claim 1, wherein the drug part further has a drug carrier carrying the hemostatic agent, and the drug carrier is a biodegradable material capable of softening at a body temperature.

10. An introducer sheath comprising:
a catheter body configured to be percutaneously introduced into a biological lumen;
a hub configured to be connected to a proximal side of the catheter body;
a drug part having a hemostatic agent capable of treating a wound site in biological tissue, and wherein the drug part is disposed on a proximal side of an outer surface of the catheter body;
a strain relief covering a distal portion of the hub and surrounding a predetermined range of the proximal side of the catheter body, and wherein the drug part is disposed in the predetermined range of the catheter body surrounded by the strain relief; and
a groove portion recessed toward an inner space of the catheter body, the groove portion being provided over the entire circumference of the outer surface of the catheter body in a range closer to the proximal side of the catheter body than a most distal portion of the strain relief and closer to a distal side of the catheter body than the distal portion of the hub.

11. The introducer sheath according to claim 10, further comprising:
a hydrophilic lubricating layer for providing surface lubricity during wetting is disposed on the outer surface of the catheter body, and wherein at least a part of the hydrophilic lubricating layer covers a distal portion of the drug part.

12. The introducer sheath according to claim 10, wherein the drug part further has a drug carrier carrying the hemostatic agent, and the drug carrier is a biodegradable material capable of softening at a body temperature.

13. A method for treating a wound site resulting from treatment of a biological lumen, the method comprising:
introducing the introducer sheath according to claim 1 into the wound site of a patient;
placing the catheter body in the biological lumen in a state where the drug part is not disposed at the wound site;
performing a desired treatment by introducing a treatment instrument into the biological lumen via the introducer sheath in a state where the drug part is not disposed at the wound site and the catheter body is placed at the wound site;
bringing at least a part of the drug part into contact with the wound site by moving the catheter body toward the wound site after the desired treatment is completed; and
placing the at least a part of the drug part at the wound site.

14. The method according to claim 13, further comprising:
exposing the drug part by removing the strain relief from the catheter body before the bringing the at least a part of the drug part into contact with the wound site.

15. The method according to claim 14, further comprising:
when the proximal side of the introducer sheath is moved toward the wound site, introducing the dilator through a hemostatic valve of the introducer sheath, and moving the introducer sheath in a state where the dilator is inserted in the lumen of the introducer sheath; and
exposing the drug part either before or after the insertion of the dilator through the hemostatic valve of the introducer sheath.

16. A method for treating a wound site resulting from treatment of a biological lumen, the method comprising:
- introducing the introducer sheath according to claim 6 into the wound site of a patient;
- performing a desired treatment by introducing a treatment instrument into the biological lumen via the introducer sheath in a state where the drug part is not disposed at the wound site and the catheter body is placed at the wound site;
- bringing at least a part of the drug part into contact with the wound site by moving the catheter body toward the wound site after the desired treatment is completed;
- placing the at least a part of the drug part at the wound site; and
- wherein the introducer sheath includes a cover member covering the drug part, and wherein the drug part is disposed on the proximal side of the outer surface of the catheter body and outside the strain relief, the introducing of the drug part into the wound site comprises:
- exposing the drug part by removing the cover member from the drug part before the bringing the at least a part of the drug part into contact with the wound site.

17. The method according to claim 16, further comprising:
- when the proximal side of the introducer sheath is moved toward the wound site, introducing the dilator through a hemostatic valve of the introducer sheath, and moving the introducer sheath in a state where the dilator is inserted in the lumen of the introducer sheath; and
- exposing the drug part either before or after the insertion of the dilator through the hemostatic valve of the introducer sheath.

18. The method according to claim 13, wherein the placing of the at least a part of the drug part at the wound site comprises:
- withdrawing the introducer sheath from the biological lumen while the wound site is pressed against the drug part, and rubbing and/or scraping off the drug part at the wound site in conjunction with the withdrawal operation for the introducer sheath.

19. The method according to claim 13, further comprising:
- performing hemostatic state maintenance after the withdrawal of the introducer sheath with a bandage.

* * * * *